(12) United States Patent
Rabie

(10) Patent No.: US 7,943,187 B2
(45) Date of Patent: May 17, 2011

(54) PAEONIFLORIN PREPARATIONS AND USES THEREOF FOR FAT REDUCTION

(75) Inventor: Bakr Rabie, Hong Kong (CN)

(73) Assignee: Bakr Rabie

(*) Notice: Subject to any disclaimer, the term of this patent is extended or adjusted under 35 U.S.C. 154(b) by 219 days.

(21) Appl. No.: 12/126,246

(22) Filed: May 23, 2008

(65) Prior Publication Data

US 2009/0292238 A1    Nov. 26, 2009

(51) Int. Cl.
*A61K 36/00* (2006.01)
(52) U.S. Cl. .................. 424/779; 424/778; 424/725
(58) Field of Classification Search .............. None
See application file for complete search history.

(56) References Cited

U.S. PATENT DOCUMENTS

| | | | | |
|---|---|---|---|---|
| 5,698,199 | A | * | 12/1997 | Mori et al. .......... 424/734 |
| 2006/0074355 | A1 | * | 4/2006 | Slayton et al. .......... 601/2 |
| 2008/0294072 | A1 | * | 11/2008 | Crutchfield, III .......... 601/2 |

FOREIGN PATENT DOCUMENTS

| | | | |
|---|---|---|---|
| EP | 1021191 | | 7/2000 |
| EP | 1748780 | | 2/2007 |
| JP | 2004-217583 | * | 5/2004 |
| WO | WO 9917712 | | 4/1999 |
| WO | WO2005112942 | | 12/2005 |

OTHER PUBLICATIONS

"What is Peony?", evitamins.com/healthnotes.asp?ContentID=3658006-.*
Duncan, D. I. and F. Hasengschwandtner (2005). Aesthetic Surgery Journal 25(5): 530-543.
Hexsel, D., M. Serra, et al. (2003). J Drugs Dermatol 2(5): 511-8.
Hexsel, et al (2005) Otolaryngologic Clinics of North America, 38(5):1119-1129.
Jenning, et al (2000) *International Journal of Pharmaceutics* 199(2): 167-177.
Jones, et al (1999) *International Journal of Pharmaceutics* 177(2): 137-159.
Le Maire, et al (2000) *BBA-Biomembrances* 1508 (1-2): 86-111.
Lombardi, et al (2005) *Journal of Controlled Release* 110(1): 151-163.
Navder (1997) *Life Sciences* 61(19): 1907-1914.
Rittes, P. G. (2001). Dermatologic Surgery 27(4): 391-392.
Guedes Rittes, P. (2003). Aesthetic Plastic Surgery 27(4): 315-318.
Rose, et al (2005) Journal of Cosmetic and Laser Therapy, 7(1):17-19.
Rotunda, A. M. (2004). Journal of the American Academy of Dermatology, P160, Abstract P624.
Rotunda, A. M., H. Suzuki, et al. (2004). Dermatologic Surgery 30(7): 1001-1008.
Salti, et al (2007) *Dermatologic Surgery*, 34(1):60-66.
Schafer-Korting, et al (2007) *Advanced Drug Delivery Reviews* 59(6): 427-443.
Vedamurthy (2007) *Indian J Dermatol Venereol Leprol* 73(1): 60-2.
Wissing, et al (2001) *Pharmazie* 56(10): 783-6.

* cited by examiner

*Primary Examiner* — Christopher R Tate
*Assistant Examiner* — Deborah A. Davis
(74) *Attorney, Agent, or Firm* — Denise L. Mayfield; Katten Muchin Rosenman LLP

(57) ABSTRACT

Disclosed are methods and preparations useful for reducing fat at a targeted area(s) on a human. The preparations comprise as an active ingredient an adipolysis enhancing (i.e., fat-melting) amount of an active ingredient, paeoniflorin (PF). The preparations may be provided as an injectable preparation or as a topically applied preparation, such as in the form of a crème or lotion. In topical preparations, the active ingredient paeoniflorin may be contained within nanospheres, such as albumin nanospheres. The PF-containing preparations may also include a permeant, such as azone. The method may be accompanied by the application of ultrasound to the area being treated prior to, during or after, or prior to, during, and after application of the paeoniflorin preparation to an area of the body in which fat reduction is desired. By way of example, the methods and preparations are effective for reducing targeted fat deposits at various anatomical sites of the body, such as the midsection ("love handles"), jowls, hips, arms, thighs and buttocks area.

5 Claims, 13 Drawing Sheets

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 1
gctggtgcag agagacac                                                   18

<210> SEQ ID NO 2
<211> LENGTH: 18
<212> TYPE: DNA
<213> ORGANISM: Artificial Sequence
<220> FEATURE:
```

```
<223> OTHER INFORMATION: Description of Artificial Sequence:
      Synthetic primer

<400> SEQUENCE: 2
gaaagcagcg cgcacgcg                                               18
```

PAEONIFLORIN PREPARATIONS AND USES THEREOF FOR FAT REDUCTION

BACKGROUND

Supplements, medicines and other products that promote fat loss continue to be in great demand. Products suitable for reducing fat in target areas including the thighs, stomach and midsection ("love-handles"), are of particular interest. However, existing fat loss products are incapable of accomplishing this result, and routinely require strenuous diet and exercise to accomplish the desired results. Most fat loss products facilitate only a general fat loss across the body, rather than in specific, targeted areas. A significant amount of time and effort is typically required in order to accomplish even modest, non-target specific weight loss.

An ever-growing percentage of the population continues to grow more and more overweight. The absence of effective and safe over-the-counter weight-loss products has created an ever growing need for alternative, more effective methods for weight and/or fat control. Preferably, an improved weight loss product that satisfies these needs would closely mimic natural fat loss processes and target typical "fat-zone" prone areas. Such a product would typically also include a user-friendly delivery device(s) to further enhance administration of the product to a targeted body area to reduce stored fat deposits under the skin.

These factors evidence a continuing and growing medical need for safe and effective non-prescription preparations for facilitating fat and/or weight loss, particularly targeted fat and/or weight loss.

SUMMARY

The present invention satisfies these and other needs in the art.

In one aspect, a method is provided for enhancing fat loss in an animal particularly a human, by administering a preparation and/or composition comprising as an active ingredient paeoniflorin (PF), which is a natural, purified bioactive glucoside in Paeonial Radix (PR). PF may be further described as comprising a natural, purified bioactive glucoside isolated from Paeonial Radix (PR), the roots of Paeonia Pall. In some aspects, the composition may be further described as comprising an adipolysis promoting amount of paeoniflorin (PF)

An adipolysis promoting amount of active ingredient comprising paeoniflorin (PF):

Triglycerides:

In a general and overall sense, the fat-burning, or adipolysis promoting activity of the present preparations/compositions is provided by the activity found to exist in particular preparations and/or formulations of PF for inducing the expression of β-adrenergic receptors present on fat cells. This results, among other fat break-down promoting events, in a reduction in fat stores that closely resembles the physiological and biochemical events that are known to occur during natural fat loss. One of the clinical indicators of the physiological events associated with fat breakdown is a decrease in detectable plasma levels of triglycerides. The breakdown of triglycerides results in the breakdown products of glycerol and fatty acids. Thus, a clinical indication of fat breakdown in a patient may be a reduction and/or lower plasma level of triglycerides. Triglycerides in the blood plasma of a patient may thus be monitored in a plasma sample from a patient as an indicator and/or monitoring event of fat break down.

In some embodiments, an adipolysis promoting amount of PF may be described as an amount of PF that is sufficient to provide an increase in the amount of glycerol released in a culture of 3T3-L1 adipocytes in the presence of an adipolysis enhancing amount of PF, compared to the amount of glycerol released by 3T3 adipocytes in culture media without the same amount of PF. By way of example, an adipolysis enhancing amount of PF may be an amount of about 1 umol/L to about 5 umol/L of the PF preparation and/or composition.

In clinical studies, it is shown herein that a decrease in blood plasma triglycerides is detectable upon treatment of the patient with PF, and is evidence of fat breakdown. In a particular embodiment, a reduction in plasma levels of triglycerides, and hence fat breakdown, results upon treatment of a patient with multiple, relatively small injections of PF within an area of a patient's fat stores with a total dose of about 0.5 mg PF, each injection site receiving about 0.025 mg PF in a volume of about 0.5 ml injection grade water/Phosphatidyl choline.

cAMP Levels:

The natural fat break-down achieved with the present compositions/preparations may also be characterized by the increase in cAMP levels that result as a consequence of treatment. Thus, in some embodiments, an adipolysis promoting amount of PF may be described as an amount of PF that is sufficient to increase levels of cAMP in a culture of 3T3 adipocytes, compared to cAMP levels in a culture of 3T3 adipocytes without the same amount of PF. By way of example, the amount of PF that will increase cAMP levels is about 11 moles/Liter.

Hormone Sensitive Lipase (HSL):

The natural fat break-down achieved with the present compositions/preparations may also be characterized by the increase in hormone sensitive lipase (HSL) levels that result as a consequence of treatment with PF. Thus, in some embodiments, an adipolysis promoting amount of PF may be described as an amount of PF that increases detectable amounts of hormone sensitive lipase (HSL) in a culture of 3T3 adipocytes, compared to hormone sensitive lipase (HSL) levels in a culture of 3T3 adipocytes without the same amount of PF. In some embodiments, this may be described as an amount of PF that increases expression of a gene encoding hormone sensitive lipase (HSL). By way of example, the amount of PF that increases detectable amounts of hormone sensitive lipase in a culture of 3T3 adipocytes compared to the amount of hormone sensitive lipase detectable in a culture of 3T3 adipocytes without PF is about 1 mmol/Liter.

Adipolysis-Promoting Ratio of Adrenergic Receptor (AR) Expression (lipolysis greater than lipogenesis), β-adrenergic receptors/a2b-adrenergic receptor expression ratio.

The natural fat break-down achieved with the present compositions/preparations may also characterized by the increase in expression levels of β-adrenergic receptors that result as a consequence of treatment. Therefore, in some embodiments, the adipolysis promoting amount of PF may be described as an amount of PF that is sufficient to provide a lipolysis enhancing ratio of adrenergic receptor expression, relative to lipogenesis enhancing adrenergic receptor expression in a culture of 3T3 adipocytes without or absent the same amount of PF. By way of example, the lipolysis enhancing adrenergic receptors include Adrb1, Adrb2 and Adrb3, while the lipogenesis enhancing adrenergic receptors include a2B-AR.

Generally, PF would be provided in an amount that would elicit a lipolysis enhancing ratio of adrenergic receptor expression. By way of example, this amount would comprise an increase in the ratio of β-adrenergic receptor expression relative to a2b-adrenergic receptor expression. This amount of PF may further be described as an amount that results in an increase in 3-fold to about 7 or 8-fold expression of the lipolysis enhancing adrenergic receptors, relative to the expression level of a2b-adrenergic receptors.

Adiponectin Receptor (Adipor1):

The natural fat break-down achieved with the present compositions/preparations may also be characterized by a decrease in expression levels of adiponectin receptor (Adipor1) that results as a consequence of treatment. Therefore, and in some embodiments, the adipolysis promoting amount of PF may be described as an amount of PF that is sufficient to provide a decrease or reduction in the expression of Adipor1 in a culture of 3T3 adipocytes relative to the amount of Adipor1 expression in a culture of 3T3 adipocytes without the same amount of PF.

Obesity-Related Gene Panel:

Carboxypeptidase E gene (Cpe gene), peroxisome proliferator activated receptor gamma gene (Pparg, a regulator of adipocyte differentiation), adrenergic receptor genes (such as Adrb2, Adrb3) and Adiponectin receptor 1 gene (Adipor1) are among some of the obesity-related genes that comprise the obesity-related gene panel as described herein.

In these embodiments, an adipolysis promoting amount of PF may be described as an amount of PF that increases the expression level of a panel of obesity-related genes relative to the expression level of the same panel of obesity-related genes in the absence of the same amount of PF. In some embodiments, the expression level of the obesity-related gene panel is increased about 1.5 fold, compared to the expression level of this obesity-related gene panel in a culture of 3T3 adipocytes without this amount of PF.

By way of example, one of the genes that is an obesity-related gene as described in the present methods and compositions is the gene encoding carboxypetidase E (Cpe). In particular, an adipolysis promoting amount of PF may be described as an amount of PF that increases the expression level of a Cpe gene by 3T3 adipocytes, compared to the expression level of Cpe gene in a culture of 3T3 adipocytes without the same amount of PF. By way of example, the amount of PF that increases the expression level of Cpe gene by 3T3 adipocytes is an amount that will increase expression levels of Cpe gene 2 to 3 fold compared to the expression level of Cpe gene in a culture of 3T3 adipocytes without this amount of PF. In some embodiments, this amount of PF is about 1 umol/Liter.

Type of Delivery/Application Formulation:

In various aspects of the method, the preparation comprising the active ingredient PF may comprise PF in a concentration that is effective to penetrate the skin and into fat cells, such as to a subcutaneous (i.e., just under the skin) deposit of fat cells. The PF will thus be provided in any variety of application modalities to provide an effective fat cell penetrating concentration of PF to a targeted fat area. This fat cell penetrating concentration of the active ingredient, PF, is further described as an adipolysis promoting amount of PF. The adipolysis promoting amount of the PF as a component of a preparation and/or composition will be determined, at least in part, by the form of the particular formulation (i.e., topical, injectable, etc.) as provided to the targeted fat deposit area(s).

Where the preparation and/or composition is administered topically, such as in a crème and/or lotion, the adipolysis promoting amount of the PF will be a concentration comprising about 0.2 mg to about 0.3 mg per ml of the crème and/or lotion. The application of the crème and/or lotion, by way of example, may then be followed by the application of a weak electrical current to the area.

In those embodiments where the preparation is in the form of a crème and/or lotion, the preparation may further comprise, for example, a permeant. Virtually any of a variety of permeants may be used in conjunction with the topical preparations of the invention. By way of example, such a permeant may comprise a permeant comprising azone. A permeant is described as an ingredient that will assist in the ability of the active ingredient PF to cross over and into the fat cells of the patient fat area being treated.

Alternatively, the formulation as a crème and/or lotion may in some embodiments comprise albumin nanospheres. In this form, the preparation would be applied to a desired area, followed by subjecting the area to ultrasound. In this way, the albumin nanospheres in the composition crème and/or lotion will be driven though the skin to the fat cells by the action of the ultrasound.

In those embodiments where the preparation is a preparation suitable for injection, the preparation may be described as comprising a physiologically compatible carrier solution, such as saline and/or injectable grade water. In other embodiments, the injectable preparation will further include phosphatidylcholine, or other similar phospholipids or combination of phospholipids.

By way of further example, where the preparation and/or composition is to be administered as an injectable preparation, an adipolysis promoting amount of PF may be described as an amount that delivers about 0.02 mg of the PF per 0.5 ml. injection fluid.

In another aspect, a method of treating an animal to reduce fat areas and/or to increase and/or enhance adipolysis is provided. As part of an embodiment of the method, the injectable solution of the PF-containing composition and/or preparation is delivered subcutaneously and/or subdermally to a target area of a patient at an injection site or sites spaced at least about 1 cm or so between injection sites on the patient target area being treated. Where the preparation and/or formulation is to be injected, the method may first provide for the application of a topical anesthetic to the area, such as an anesthetic gel (lignocain ointment or lidocain gel) for about 5 minutes prior to injection, to numb an area that will receive one or more injections. The skin is first wiped with an alcohol swap, 2 minutes or so later, a local anesthetic ointment such as gel anesthetic, is then rubbed on the surface area to be injected. Five (5) minutes later, the contents of a 10 ml syringe containing the PF injectable solution is then injected into about 20 injection sites on the patient fat area being treated, with 0.5 ml. of the injectable PF solution being injected subcutaneously at each injection site.

It is further contemplated that the formulations and/or preparations may be provided to a fat deposit area in any one or combination of these treatment forms suitable for achieving the desired results. In areas with large fat deposits, such as the stomach area or midsection ("love handles"), the concentration of PF may need to be increased in the injectable solution preparation. For example, it is contemplated that 1 mg of PF per 5 ml of injectable water will be prepared.

In another aspect, the preparation and/or composition will comprise as an active ingredient a component PF having the following Formula I:

Formula 1:

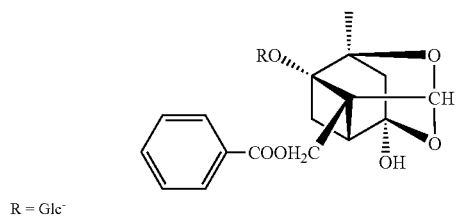

R = Glc⁻

Wherein R is a monosaccharide. In some embodiments, the monosaccharide is glucose (Glc), galactose (Gal), or other monosaccharide. In particular embodiments, the monosaccharide is glucose (Glc). In some embodiments, the glucose may be described as the D-glucose stereoisomer of glucose.

The preparations and/or compositions may also further comprise other ingredients recognized by those of skill in the pharmaceutical arts for improving delivery, stability of the formulation (shelf life), consistency, dispersion on the skin surface, scent, color, etc. By way of reference, such formulation techniques and additives are described in Remington: The Science and Practice of Pharmacy, ALFONSO R. GENNARO, 20th Edition. Baltimore, Md.: Lippincott Williams & Wilkins, 2000. This reference insofar as these teachings are concerned is hereby specifically incorporated by reference.

The PF was purchased in a commercial purified dry form (powder) from a commercial vendor.

In other aspects, methods of reducing the size and/or dimensions of targeted adipose (i.e., fat) stores and/or adipose tissue deposits are provided. In some embodiments, this method comprises administering an adipolysis promoting amount of a preparation and/or composition comprising an adipolysis enhancing amount of an active ingredient, PF, to a targeted fat deposit area on a patient. The preparation may be administered one or more than one time, such as in part of an injection protocol, until a desired reduction in a targeted fat deposit is observed.

The injection protocol may comprise 10, 20, 30 or more than 30 individual injections per session, and include 1, 2, 3 or more sessions of such a regimen until the desired results are achieved. In some embodiments, a session of treatment provides for 20 injections. On average, it is demonstrated that a noticeable reduction in measurable fat dimensions may be observed after 4 sessions of 20 injections each (20 injections constituting one session) to 5 sessions of 20 injections. In some embodiments, about 0.025 mg PF is provided in a volume of about 0.5 ml of a carrier (such as sterile water, etc.) to each of 20 different injection sites on a patient as part of a single treatment session.

On average, a fat loss of about 3 cm may be achieved after 5 sessions of the injection series with the PF injectable preparations. In humans, the present preparations of PF provide for reducing or melting away about 1 cm of fat in stomach and thigh areas per 1 to 1.5 sessions, and about 1 cm of fat in the upper arms area per session. The methods also provide for a reduction in total cholesterol blood levels. In particular, a significant reduction in serum cholesterol, LDL cholesterol, and serum triglycerides was observed upon treatment with the herein described PF treatment methods in humans.

As part of the provided methods, a treated patient animal would be encouraged and/or required to walk and/or exercise. By way of example, such may include a brisk walk of from 25 to 30 minutes per day, for a period of seven (7) or more days. In addition, the patient animal should further drink two (2) or more liters of water for the same period of time as the walking and/or exercise regime, to maximize the slimming effect of the treatment and to facilitate flushing of broken-down fat products out of the body.

By way of example, it is envisioned that an area on a patient that would be targeted as part of the method would include the thighs, hips, chin, jowls, stomach, midsection ("love-handles"), or any combination of these areas at the same time or sequentially in any order desired.

In yet other aspects, a device suitable for the treatment of a patient animal to achieve fat loss is provided. By way of example, such a device may comprise a syringe-like device having attached thereto a needle suitable for injection into a tissue (See FIG. 11).

The device in some embodiments will thus take the form of a syringe, such as a graduated barrel syringe cylinder capable of holding a volume of a solution comprising PF, and a needle suitable for receiving one end of the graduated syringe cylinder. In particular embodiments, the needle will be configured to be at a 90° angle relative to the syringe cylinder. In some embodiments, the graduated barrel cylinder will have a volume capacity of 50 ml or more. In some embodiments, a 23×1¼" 0.65×32 mm needle may be used with a 25 ml "Slip Tip" non-lock syringe for administering the PF injectable preparations of the present methods and kits.

The present invention, in yet another aspect, provides a kit that comprises the fat-melting, fat-reducing preparations as described herein. In some embodiments, the kit may comprise 1 ml ampule or ampules of PF and azone at a concentration of 0.2 mg/ml and a device suitable for stimulating the entry of the PF in solution into fat cells of a localized fat deposit on a patient. For example, such a device is the Alpha Wave healthtronic muscle stimulator. This small device is typically and routinely used by physiotherapist to stimulate muscles after a sports injury by passing a low density current that causes muscle contraction. Due to the low voltage current of about 2.5 amp, a current will be transmitted that will drive the PF through the skin and into the adipose tissue after the azone disrupts an organized lipid layer.

By way of example, and not limitation, the following are among some of the many advantages and features of the present preparations and methods:

1. Acts directly on fat cells and dissolves fat in a manner that mirrors the physiologic fat loss.
2. Burns fat through activating receptors present on the fat cells in the target area, responsible for triggering the intracellular cAMP pathway, PKC and HSL to dissolve fat naturally.
3. Increases the number of cellular receptors responsible for burning fat.
4. Breaks fat down into its natural byproducts.
5. Noninvasive, painless and area specific.

Many points of distinction exist between the present formulations and methods for fat reduction and other methods described in the art. For example, while previous methods depend in part or whole on achieving some level of appetite suppression or inhibition of fat absorption from the gut, the present formulations and methods do not.

In addition, the present methods/formulations for fat loss are distinct and superior in many ways to mesotherapy. Mesotherapy is the use of intra- or subcutaneous injections containing mixtures of compounds to treat local medical and cosmetic conditions, and does not provide a treatment for any particular condition. It primarily involves a method of drug delivery (Rotunda and Kolodney 2006), with the compounds used in mesotherapy comprising phosphatidylcholine (a compound derived from soy, and is a component of cell membranes in humans/other organism) mixed with deoxycholate (bile salt), and may further be mixed with aminophyline. Through the use of punch biopsies taken at one and two week time points after treatment with mesotherapy, a loss in subcutaneous fat was reported. The subcutaneous fat loss was postulated to have been accomplished by emulsifying fat deposits via an inflammatory necrosis and resorption (Rose and Morgan, 2005). In contrast, and among other distinctions, the present methods provide for fat loss in a manner that mimics physiological fat break down, such as by break down into fat's natural byproducts, such as glycerol, via increase in a physiological second messenger molecule, cyclic AMP.

Additional features and advantages are described herein, and will be apparent from, the following Detailed Description and the figures.

BRIEF DESCRIPTION OF THE FIGURES

FIG. 3B, PF is shown to increase the expression of HSL in 3T3-L1 from the $3^{rd}$ day of exposure, which follows the increase of cyclic AMP and gives rise to release in glycerol as a byproduct of fat metabolism.

DETAILED DESCRIPTION

Figure 1:
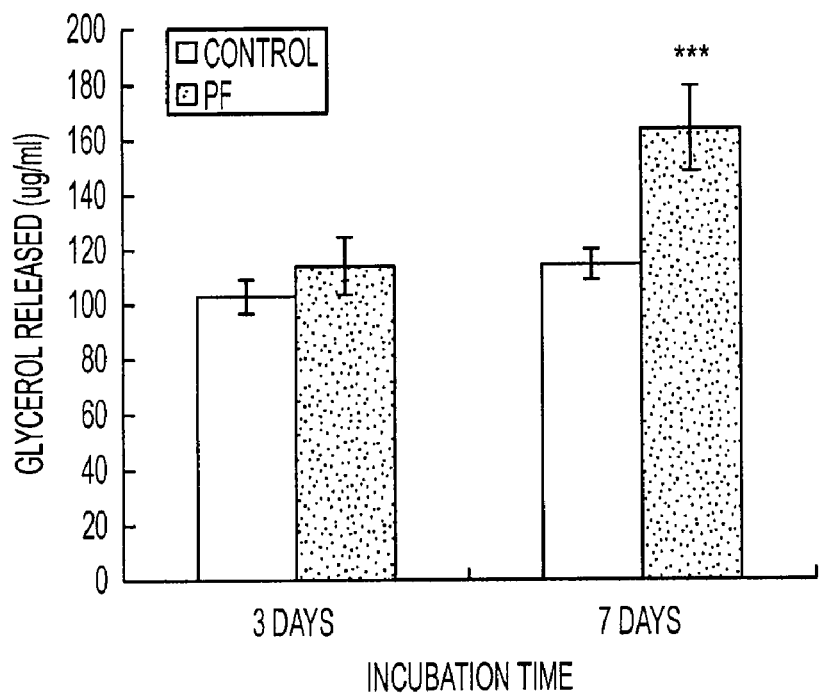
FIG. 1 demonstrates PF increased the release of glycerol by 3T3-L1 adipocytes significantly by the $7^{th}$ day after exposure FIG. 2 demonstrates intracellular cAMP tested by ELISA after incubation with PF in 3T3-L1 adipocytes.

The present invention, in a general and overall sense, provides a variety of preparations and methods for enhancing lipolysis and fat reduction and/or loss in vivo in a patient animal. The preparations and/or compositions include as an active ingredient PF. PF is a natural, purified bioactive glucoside in Paeoniac Radix (PR), the roots of Paeonia Pall. PF, a natural plant extract purified to over 99%, is provided here as a natural organic potent lipolysis drug. Its mode of action is through significantly enhancing the expression of several obesity-related genes such as Adrb2, Adrb3, Cpe, Adipor1 and Pparg.

PF enhances the expression of β-adrenergic receptors 2 & 3. β-adrenergic receptor 2 is a major biolytic receptor in human fat cells. β-adrenergic receptor 3 is important in regulating thermogenesis and lipolysis in brown adipose tissue through autonomic nervous system (ANS) activity. Its biologic intracellular pathway showed that activation of β-adrenergic receptors goes through the cAMP pathway which in turn significantly enhances the level of expression of Hormone-Sensitive Lipase (HSL), to break down tri-glycerides into glycerol and fatty acids.

According to the present compositions/methods, PF significantly enhances fat loss by enhancing a fat cell's ability to burn fat into its natural by-products. PF can be administered in any of a variety of ways that accomplishes contact of the preparation with fat cells or a tissue comprising at least some fat cells. By way of example, and not limitation, the composition may be provided to an animal, such as a human, by subcutaneous injections, or by applying the preparation as a crème and/or lotion. As a crème and/or lotion, the PF may be driven through the skin to the fat cells. This may be accomplished, for example, by using a weak electric current similar to that used by a physiotherapist, or by mixing PF with albumin nano spheres and driving the mixture through the skin to the fat cells using ultrasound.

To test the effectiveness of PF on targeted fat loss, a 3T3-L1 cell line was used. The 3T3-L1 cell line provides an art-accepted model for fat loss. Fat loss is identified utilizing an in vitro adipolysis (digestion of fats) measure in a Swiss 3T3 mouse cell line. 3T3-L1 cells propagated under normal conditions have a fibroblastic phenotype. However, when treated with a combination of dexamethasone, isobutylmethylxanthine (IBMX) and insulin, 3T3-L1 cells adopt a rounded phenotype and accumulate lipids intracellularly in the form of lipid droplets.

As detailed below, PF was found to significantly increase the number of 0-adrenergic receptors (β 1, 2 and 3 subtypes) responsible for the break down of fat into its natural byproducts. The exposure of 3T3-L1 fat cells to PF causes a significant increase in the level of expression of intracellular cyclic adenosine monophosphate (cAMP) on days 1 & 3 ($P<0.01$). This is followed by a significant increase in the level of expression of Hormone-Sensitive Lipase (HSL). HSL is a multifactoral tissue lipase that plays a critical role in fat metabolism. Such a significant increase in HSL expression is followed by a significant increase in glycerol release on day 7 of exposure to PF in vitro. In vivo, lowered levels of plasma triglycerides provide a clinical indicator of fat breakdown in a patient.

The present preparations are demonstrated to posses clinical effectiveness in patients, and to provide effective site-specific lipolysis (fat breakdown) such as that stored in the midsection region ("love handles"), stomach, jowls, hips and thighs. Blood analysis and a comparison of before and after treatment with PF revealed that blood sugar levels decreased upon treatment, and low-density-lipoprotein (LDL) levels showed a tendency towards reduction, compared to pretreatment blood sugar level measures and LDL levels.

Accordingly, the present preparations, formulations, methods and techniques provide among other things, the following advantages, characteristics and features:

1. A purified, natural and effective product (PF) that dissolves fat stored subcutaneously in the adipose tissue upon direct contact.
2. A predictable mode of PF's action. PF activates the expression of β adrenergic receptors as well as other fat metabolism genes.
3. A fat-reducing product that is provided in a suitable carrier to deliver PF across the skin to the fat layers.
4. A method that employs electric current and a charged carrier to effectively deliver the preparation with the active agent, PF, to the fat cells and into the fat layers in target areas.
5. A method that delivers PF to fat cells through the use of albumin nanospheres driven through the skin by ultrasound.

In those embodiments where the preparation is a preparation suitable for injection, the preparation may be described as comprising a physiologically compatible carrier solution, such as saline and/or sterile water. In other embodiments, the injectable preparation will further include phosphatidylcholine, or any other of a variety of similar phospholipids and combinations of phospholipids.

Example 1

PF Promotes Adipolysis

The present example demonstrates the utility of the present formulations and/or preparations for promoting adipolysis, or fat break down.

The 3T3-L1 cell line is an accepted model by those of skill in the art for natural fat loss. This cell line is a substrain of Swiss 3T3 mouse cell line 3T3-L1. This cell line propagated under normal conditions has a fibroblastic phenotype. However, when treated with a combination of dexamethasone, isobutylmethylxanthine (a non-specific inhibitor of phosphodiesterases) (IBMX) and insulin, 3T3 cells adopt a rounded phenotype and accumulate lipids intracellularly in the form of fat droplets.

Differentiated 3T3-L1 adipocytes were cultured in media containing 1 umol/L PF as test group, and media without PF as control. As a result of lipolysis activity, glycerol will be generated as a result of triglyceride breakdown and released into the extracellular space. Glycerol content from 3T3-L1 adipocyte cell culture media may therefore provide an indicator of adipolysis. It was found that PF increased the release of glycerol significantly by the $7^{th}$ day after exposure (p>0.01) (FIG. 1), compared to glycerol release from 3T3-L1 adipocytes in the absence of the same amount of PF.

It was found that PF increased adipolysis within one week after stimulation was initiated. The PF preparations are thus demonstrated to induce adipolysis indirectly by causing changes in gene expression that lead to triglyceride breakdown. Further studies were carried out to define the mechanism of action of PF.

Example 2

PF Increased cAMP

Figure 2:
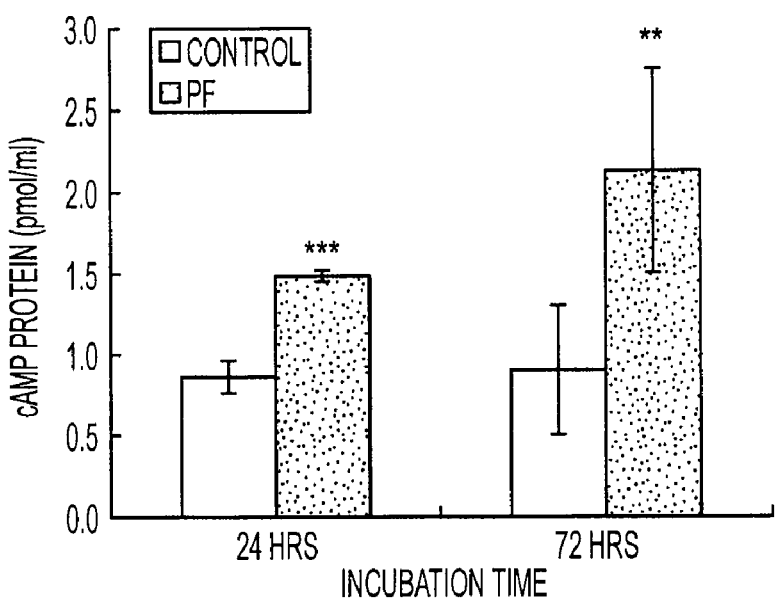

The present example, among other things, demonstrates the ability of the invention to provide effective fat loss through PF action on cyclic AMP levels. 3T3-L1 adipocytes were cultured in medium containing 11 mol/L PF as test group and medium only as control. Cells were lysed by adding 0.1 N HCL, and intracellular cyclic AMP was measured by ELISA. It was found that intracellular cyclic AMP was significantly increased by PF in the first day of exposure (P<0.001), and the third day as well (P<0.01) (FIG. 2).

The major pathway leading to lipolysis involves activation of cAMP-dependent Protein kinase A (PKA), which in turn activates other substrates such as HSL and perilipin. The agonists of β-adrenergic receptor bind to the F3-adrenergic receptor, which activates the G-protein, Gs. The activation of Gs stimulates adenylate cyclase (AC) to produce cyclic AMP. Protein kinase A (PKA) is activated by cAMP to phosphorylate the lipid droplet surface protein, perilipin (PL). Hormone-sensitive lipase (HSL) docks onto phosphorylated PL and breaks down triglyceride into glycerol and free fatty acid. Glycerol is released into the extracellular space through aquaporin adipose (AQPad). The release of glycerol was found to be increased significantly by the 7th day after PF stimulation (P<0.001), and that intracellular cyclic AMP was significantly increased by PF in the first day of stimulation (P<0.001), and the third day as well (P<0.01). The change and time-relationship of cyclic AMP and glycerol release demonstrates that PF induced adipolysis functions through the pathway of "second messenger" (cyclic AMP).

Example 3

Hormone Sensitive Lipase (HSL)

The present example demonstrates an increase in adipolysis in vivo as demonstrated by an increase in detectable levels of hormone sensitive lipase (HSL).

3T3-L1 adipocytes were cultured in medium containing 1 mol/L PF as a test group and medium only as the control group. Total RNA was extracted and reverse transcribed to cDNA employing conventional methods known to those of skill in the art.

Primers used for polymerase chain reaction (PCR) amplification of mouse HSL primers were selected based on published sequence (NM_010719) (expected PCR fragment: 409 bp):

```
                                          (SEQ ID NO: 1)
    forward primer,    5'-GCTGGTGCAGAGAGACAC-3';

(SEQ ID NO: 2)
    reverse primer,    5'-GAAAGCAGCGCGCACGCG-3'
```

Figure 3A:
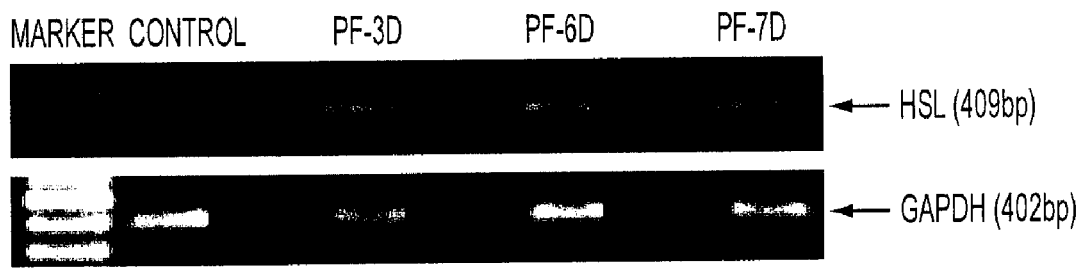
FIG. 3A-3B, demonstrates expression of HSL in 3T3-L1 adipocytes after incubation with PF.
Figure 3B:
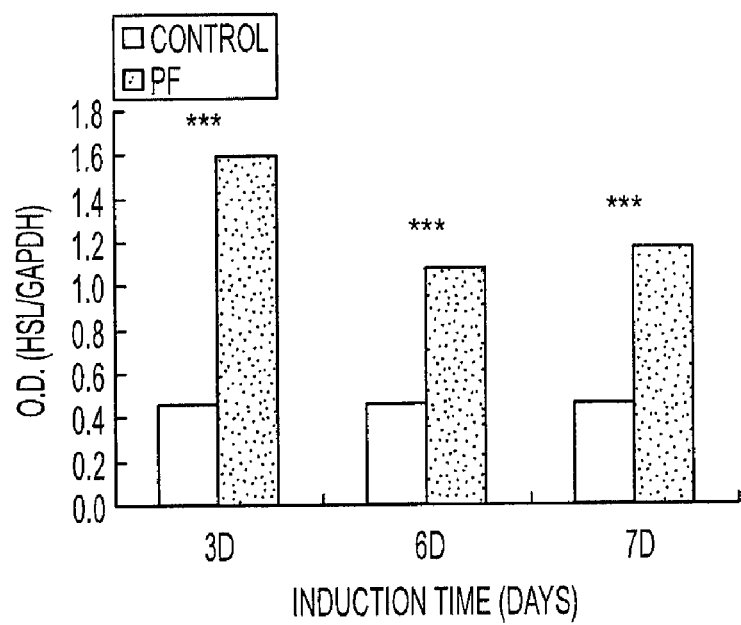

For semi-quantitative analysis, the amplification cycles were chosen within the linear range (HSL: 24 cycles with denaturation at 58° C., GAPDH: 21 cycles with denaturation at 58° C.). It was found that the PF increased the expression of HSL in 3T3-L1 cells from the third day after exposure (FIG. 3).

Hormone-sensitive lapse (HSL) is a multifunctional tissue lipase that plays a critical role in the process of fat metabolism. The enzyme has broad specificity, catalyzing the hydrolysis of tri-, di-, and monoacylglycerols, as well as cholesterol esters. HSL is thought to catalyze the major rate-limiting step in lipolysis. The lipase is acutely activated by cAMP-dependent phosphorylation, which also leads to its redistribution from the cytoplasm to the lipid droplet. Regulation of adipocyte HSL is the primary means by which lipolytic agents, such as catecholamines, stimulate the release of free fatty acids and thus control circulating levels. In this study, PF was found to increase the expression of HSL in 3T3-L1 from the third day of exposure, which follows the increase of cyclic AMP and gives rise to release of glycerol as a byproduct of fat metabolism (FIG. 4) in vitro.

Example 4

Nanosphere Formulation with PF

The present example is provided to demonstrate, by way of example only, one of the dermal preparations of PF. In particular, a nanosphere formulation with PF is presented.

Solid lipid nanoparticles (SLN) and nanostructured lipid carriers (NLC) for the topical application to the skin are made of lipids such as glycerol behenate (Compritol® 888 ATO), glycerol palmitostearate (Precirol® ATO 5), or the wax, cetyl palmitate. For NLC at room temperature, liquid lipids such as medium chain triglycerides (Miglylol® 812) are added. Alternatively, oleic acid belonging to the frequently used penetration enhancers in semisolid vehicles applied to the skin, may be added to enhance drug uptake further (Lombard Borgia, Regehly et al. 2005). Mean particle size ranges of the nanospheres was from 50 to 1000 nm. Nano dispersions contained 5 to 40% lipid. The higher concentrated preparations are of semisolid appearance, and are cosmetically acceptable as they are. Depending on the mode and concentration of the lipid, 0.5 to 5% surfactant may be added for physical stabilization of the particles. For dermal use, these are Poloxamer 188, Polysorbate 80, lecitihin, Tyloxapol®, TegoCare® 450 (polyglycerol methylglucose distearate), Miranaol®Ultra C32 (sodium cocoamphoacetate) or saccharose fatty acid ester.

To facilitate dermal application, fluid dispersions which are obtained when the lipid content is low (<10%) can be incorporated into a crème or gel base which does not induce dissolution or aggregation of SLN particles. Photon correlation spectroscopy and differential scanning calorimetry results have not changed over a storage period of 6 months (Jenning, Thunemann et al. (2000) and Wissing and Muller (2001), copied from Scafer-Korting, Mehnert et al. (2007)).

Example 5

Microarray Analysis of 111 Obesity-related Genes

The present example demonstrates that one of the clinical indicators of the fat-burning and obesity fighting activity of the present formulations and/or preparations includes an increase in the expression levels of obesity-related genes.

In order to explore a more detailed mode of action of PF on adipolysis, microarray analysis was carried out on a panel of obesity-related genes. Expression levels from this gene panel are shown to be increased by PF, compared to expression levels of these genes in the absence of PF.

3T3-L1 adipocytes were cultured in medium containing 1 umol/L PF as test group and medium only as control. Total RNA was extracted and Oligo GEArray was tested using Superarray OMM-17. The GEArray includes 111 obesity-related genes that are directly involved in the regulation of energy intake and expenditure. The genes included orexigenic peptides, hormones, and receptors, anorectic peptides, hormones, receptors, and central and peripheral signaling molecules involved in energy expenditure. The increase changes or decrease changes of more than 1.5 fold are regarded meaningful according to the diagnosis discipline, as described in the insert literature of a metabolic disease/obesity gene panel product purchased from Superarray Bioscience Corporation. (Frederick, Md.).

In the following microarray analysis, the red color shows the expression of obesity-related genes increased by more than 1.5 fold, and the blue color shows the expression of the obesity-related genes decreased by more than 1.5 fold, i.e., the number less than 0.66 shows reduction of more than 1.5 fold. In the graphs, the data above the upper line and the data below the lower line show a significant change of gene expression.

Adrenergic Receptor (AR)

Figure 5:
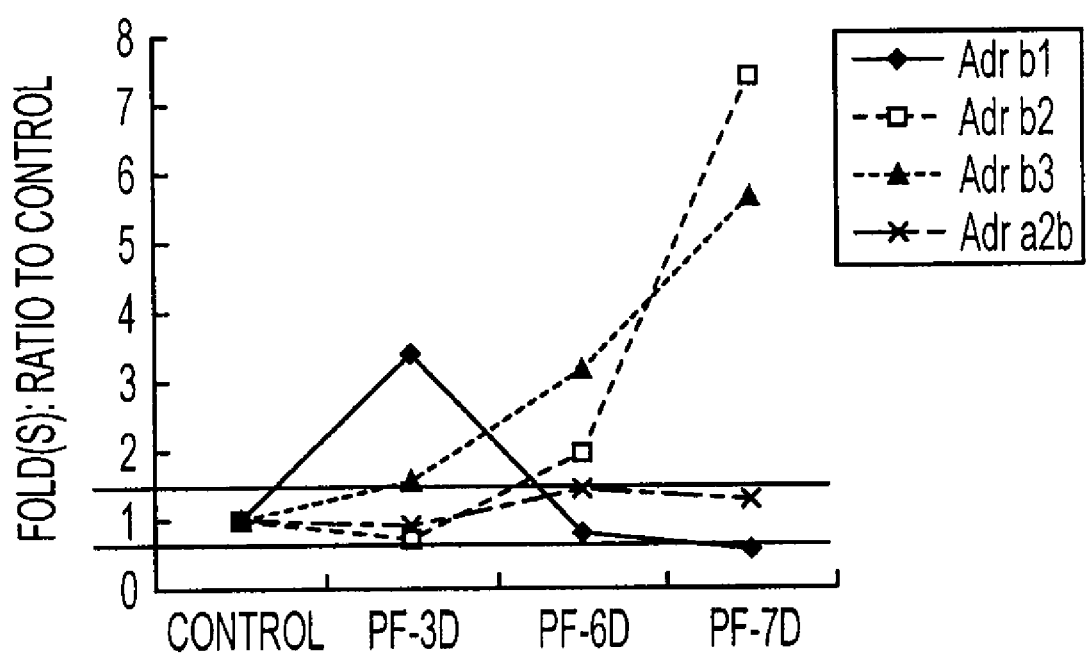
FIG. 5 demonstrates Expression of AR in 3T3-L1 adipocytes exposed to PF.

The adrenergic system plays a major role in the regulation of lipolysis in white adipose tissue, which is the major site of energy storage. Catecholamines are able to stimulate lipolysis by the activation of adipocyte 8-adrenergic receptors (131-, B2-, B3-AR). At the same time, catecholamines can also increase lipid storage through a2b-AR. Since β and a2b-AR coexist on the same fat cell, the ratio of functional a1b- and B-AR present in adipose tissue may determine whether fat storage or release is activated by catecholamines (Soloveva et al., 1997). The present data of microarray analysis after exposure to PF demonstrated a significant increase in the expression of Adrb1, Adrb2 and Adrb3, and no effect on Adra2b (Table 2, FIG. 5). Adrb1 was activated earlier followed by Adbr3 then Adbr2. Adrb2 and Adrb3 were increased by 7.4 fold and 5.65 fold, respectively, at 7 days post exposure to PF. Since the expression of Adra2b almost did not change during the whole study, while there was a significant increase in β receptor levels, that the ratio of β-adrenergic receptors to a2b-adrenergic receptors is shown to be increased by PF. In other words, lipolysis exceeds lipogenesis when exposed to PF.

Table 2. Ratio of expression signals of AR in 3T3-L1 adipocytes exposed to PF compared to control

TABLE 2

| Expression of AR in 3T3-L1 adipocytes exposed to PF | | | | |
|---|---|---|---|---|
| | Control | PF-3 days | PF-6 days | PF-7 days |
| β1-adrenergic receptor (Adrb1) | 1 | 3.39 | 0.8 | 0.58 |
| β1-adrenergic receptor (Adrb2) | 1 | 0.74 | 1.96 | 7.40 |
| β1-adrenergic receptor (Adrb3) | 1 | 1.56 | 3.18 | 5.65 |
| β1-adrenergic receptor (Adra2b) | 1 | 0.92 | 1.44 | 1.27 |

Figure 4:
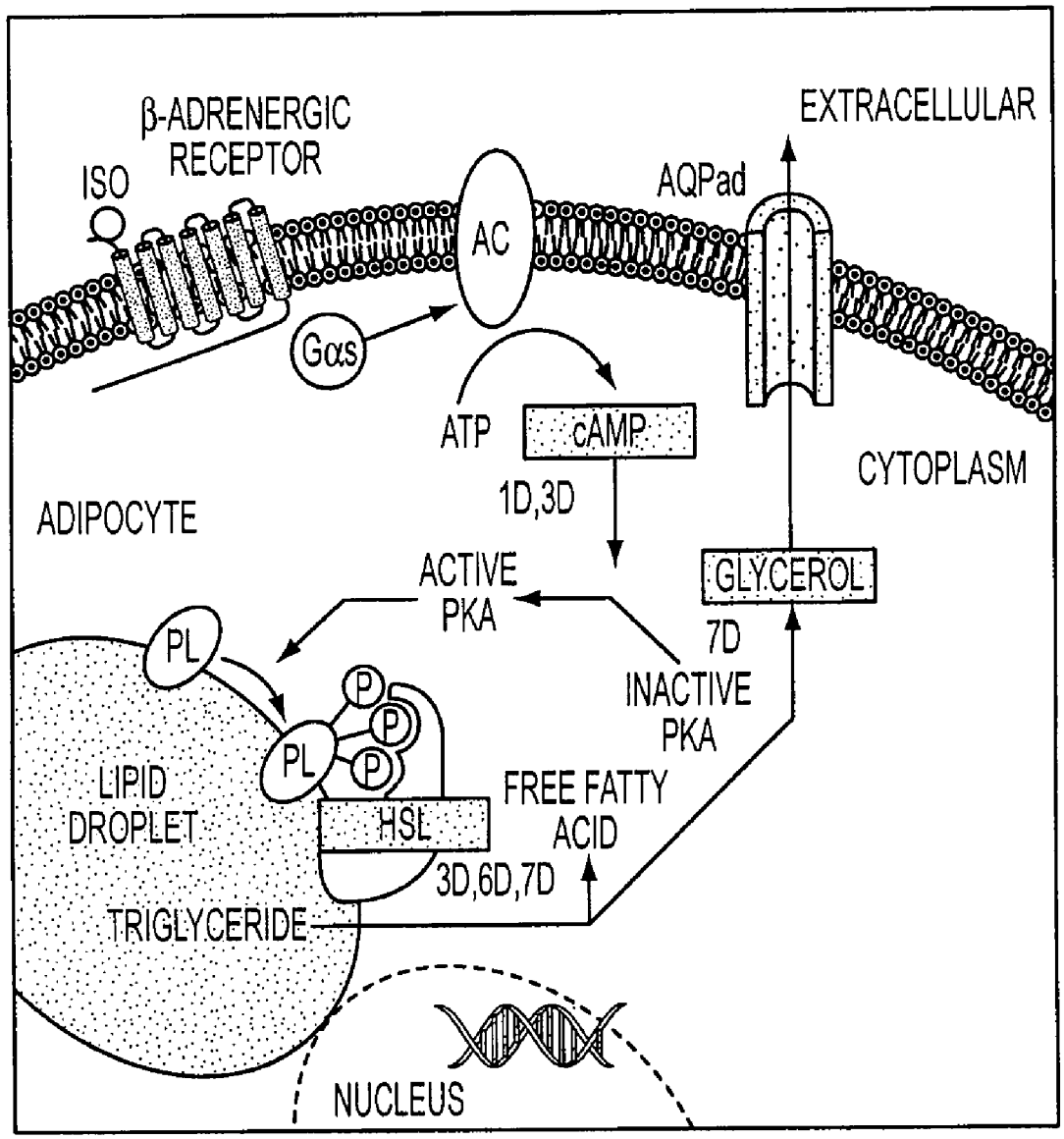
FIG. 4, demonstrates pathway of adipolysis.
Figure 6A:
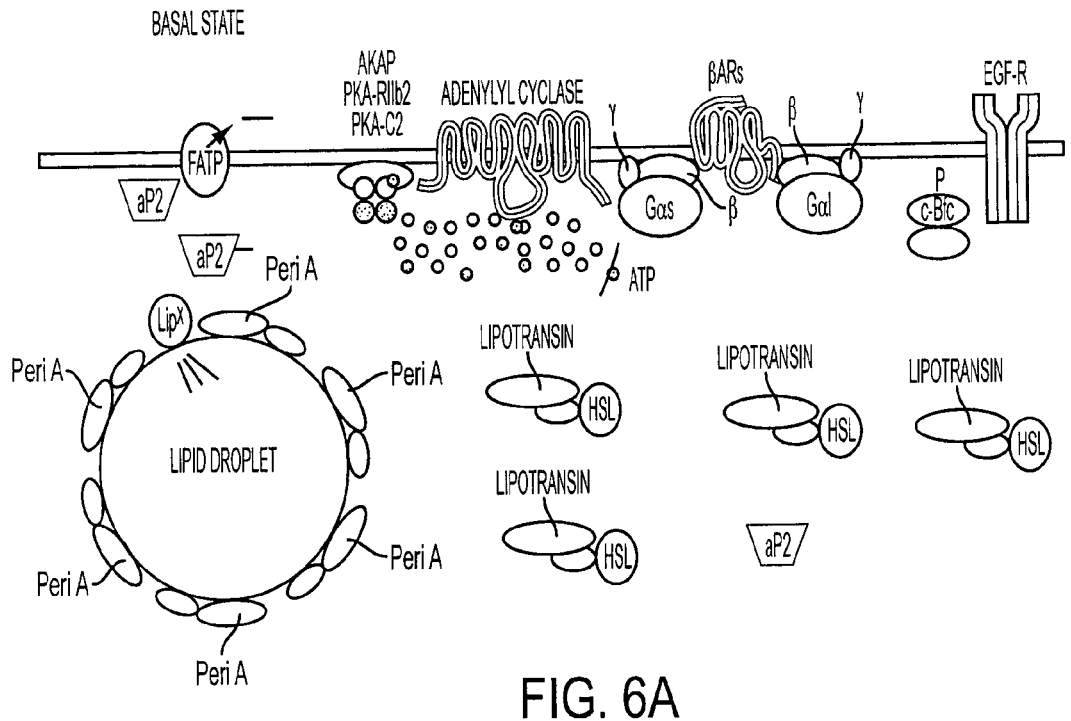
FIG. 6A-6B, demonstrates mechanisms of lipolysis stimulation by β-ARs. 6A=Basal State, 6B=Activated State.
Figure 6B:
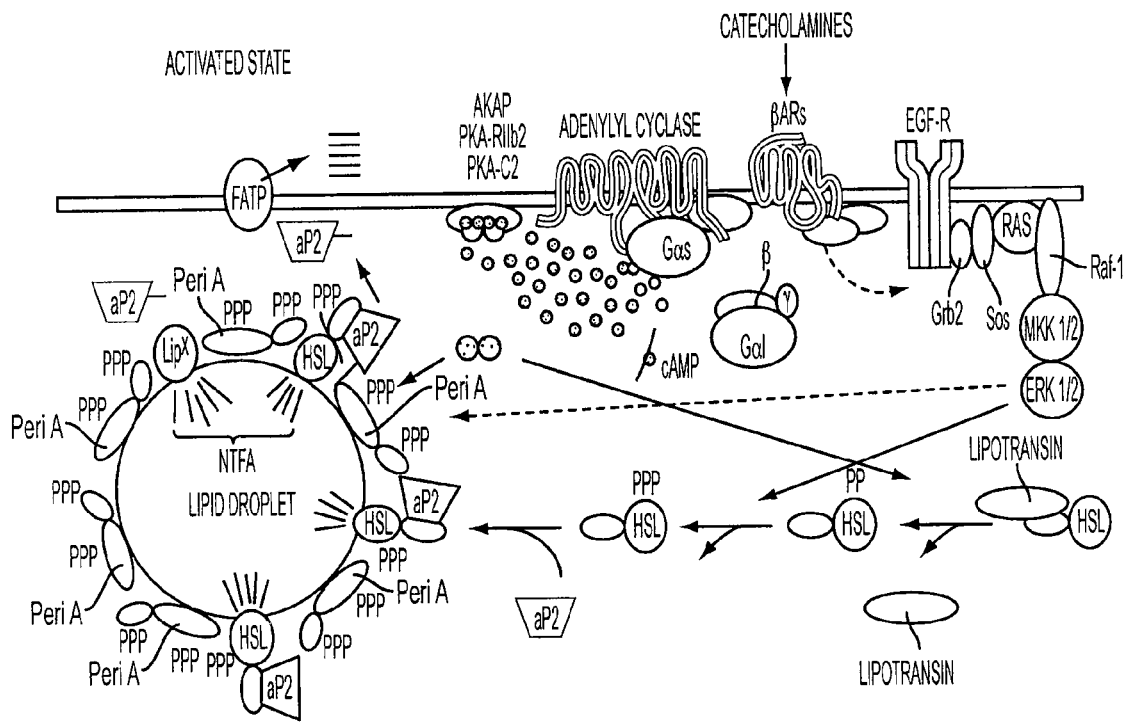

The three β-adrenergic receptor subtypes (β1-, β2-, β-AR) are members of a large family of G protein-coupled receptors, which function through the production of cAMP and the activation of HSL (Soloveva et al., 1997). In the basal state (FIG. 6A), nonphosphorylated HSL is in the cytosol probably bound to some cytosolic acceptors such as lipotransin, and nonphosphorylated perilipin (PL) is tightly bound to the lipid droplet. HSLs do not have free access to the droplet. When catecholamines interact with the β-ARs (FIG. 6B), β-ARs alternatively couple to G-protein, Gs. The activation of Gs stimulates adenylate cyclase (AC) to produce cyclic AMP. Protein kinase A (PKA) is activated by cAMP to phosphorylate the lipid droplet surface protein, perilipin (PL). Hormone-sensitive lipase (HSL) docks onto phosphorylated PL and breaks down triglyceride into glycerol and free fatty acid. Glycerol is released into the extracellular space through aquaporin adipose (AQPad) (FIG. 4).

The results of β-ARs gene expression and that of the change of cAMP and HSL (shown in part IV) mirror the pathway above.

Carboxypeptidase E (Cpe)

Figure 7:
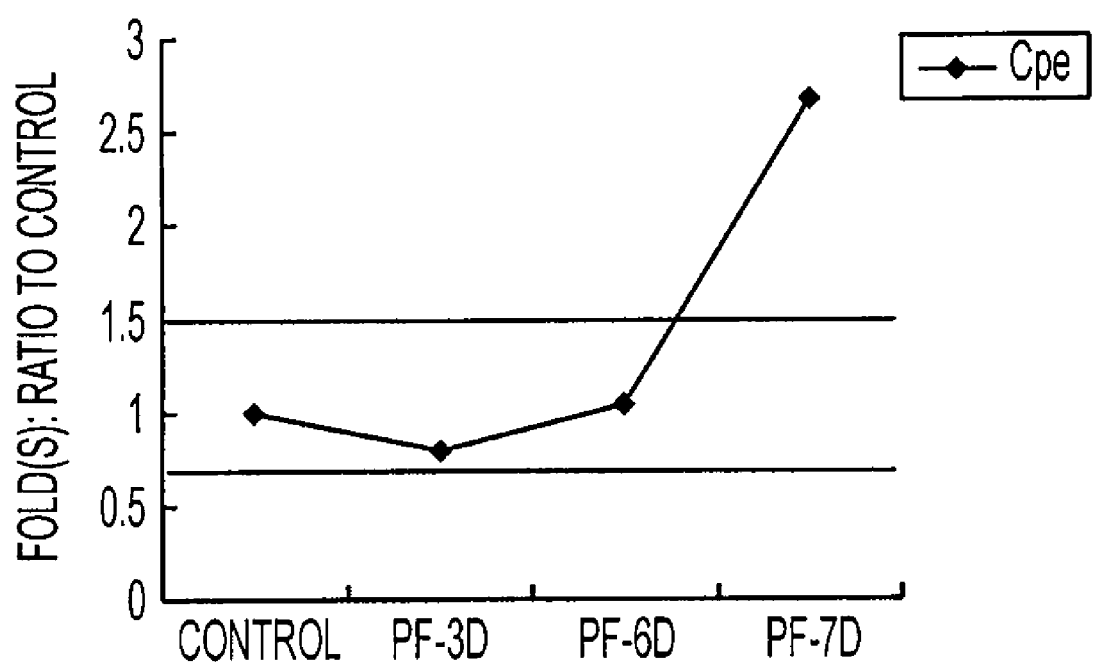
FIG. 7 demonstrates an expression of Cpe in 3T3-L1 adipocytes exposed to PF.

Carboxypeptidase E (Cpe) is a key enzyme involved in the biosynthesis of peptide hormones and neurotransmitters, including insulin. Cpe plays a vital role in fat metabolism. The mutations in the gene of Cpe result in "fat mutation" (Naggert et al., 1995). "Fat mutation" represents the first demonstration of an obesity-diabetes syndrome elicited by a genetic defect in a prohormone processing pathway (Naggert et al., 1995). The fat mutation mouse does not express Cpe and presents as obese and hyperglycemic. The present data of microarray analysis for PF demonstrated a significant increase in the level of expression of Cpe on day 7 of exposure of 3T3-L1 adipocytes to PF. The expression of Cpe was increased by 2.67 fold compared to the control (Table 3, FIG. 7).

TABLE 3

Ratio of expression signals of Cpe in 3T3-L21 adipocytes exposed to PF compared to control

| | Control | PF-3 days | PF-6 days | PF-7 days |
|---|---|---|---|---|
| Carboxypeptidase E (Cpe) | 1 | 0.79 | 1.04 | 2.67 |

Adiponectin Receptor 1 (Adipor1)

Figure 8:
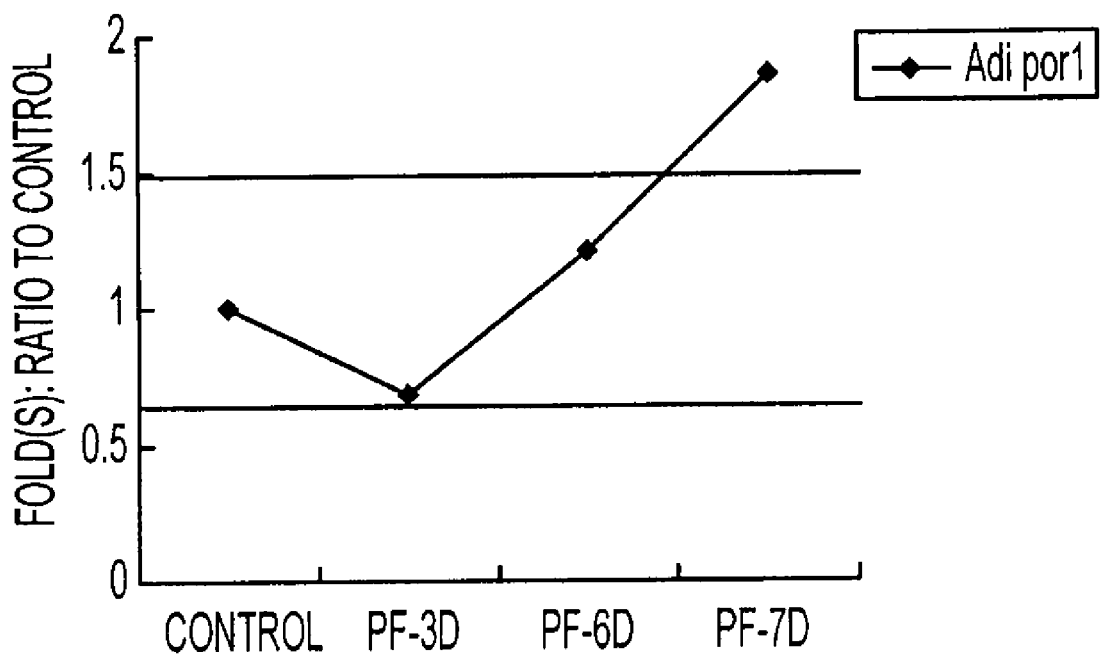
FIG. 8 demonstrates an expression of Adipor1 in 3T3-L1 adipocytes exposed to PF.

Adiponectin has been shown to increase insulin sensitivity and decrease plasma glucose by increasing tissue fat oxidation. AdipoR1 serves as receptor for globular adiponectin and mediates increased AMP-activated protein kinase, glucose uptake and fatty-acid oxidation by adiponectin (Yamauchi et al, 2003). The present data of microarray analysis revealed that the expression of Adipor1 was increased by 1.86 fold on day 7 of exposure of 3T3-L1 adipocytes to PF (Table 4, FIG. 8). Since it is proved that obesity-linked down-regulation of adiponectin is a mechanism whereby obesity could cause insulin resistance and diabetes, adiponectin receptor agonists and adiponectin sensitizers are suggested to serve as versatile treatment strategies for obesity-linked diseases such as diabetes and metabolic syndrome (Kadowaki and Yamauchi, 2005).

TABLE 4

Ratio of expression signals of Adipor1 in 3T3-L1 adipocytes exposed to PF compared to control

| | Control | PF-3 days | PF-6 days | PF-7 days |
|---|---|---|---|---|
| Adiponectin receptor 1 (Adipor1) | 1 | 0.68 | 1.21 | 1.86 |

Peroxisome Proliferators Activated Receptor Gamma (Pparg)

Figure 9:
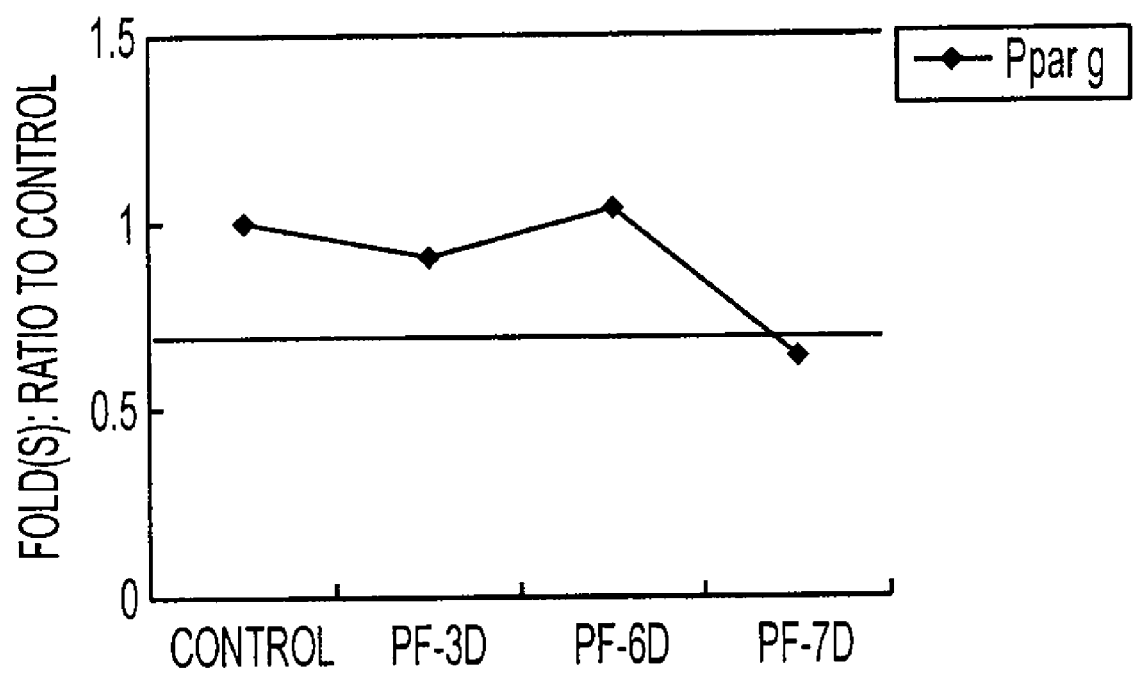
FIG. 9 demonstrates an expression of Pparg in 3T3-L1 adipocytes exposed to PF.

Pparg encoded PPAR-gamma, is a regulator of adipocyte differentiation. PPAR-gamma has been implicated in the pathology of numerous diseases including obesity, diabetes, atherosclerosis and cancer. In other words, its reduction will inhibit the differentiation of new adipocytes. It was shown by microarray that the level of expression of Pparg was reduced by 1.54 fold on day 7 of exposure of 3T3-L1 adipocytes to PF (Table 5, FIG. 9). In the microarray analysis, the blue color shows gene expression decreased by more than 1.5 fold, i.e. the number less than 0.66 shows reduction of more than 1.5 fold. In the graph, the data below the lower line shows significant reduction of the gene expression.

TABLE 5

Ratio of expression signals of Pparg in 3T3-L1 adipocytes exposed to PF compared to control

| | Control | PF-3 days | PF-6 days | PF-7 days |
|---|---|---|---|---|
| Peroxisome proliferators activated receptor gamma (Pparg) | 1 | 0.91 | 1.09 | 0.64 |

Example 6

Comparison of the Effect of PF and Meso (M) on Fat Cells

Figure 12:
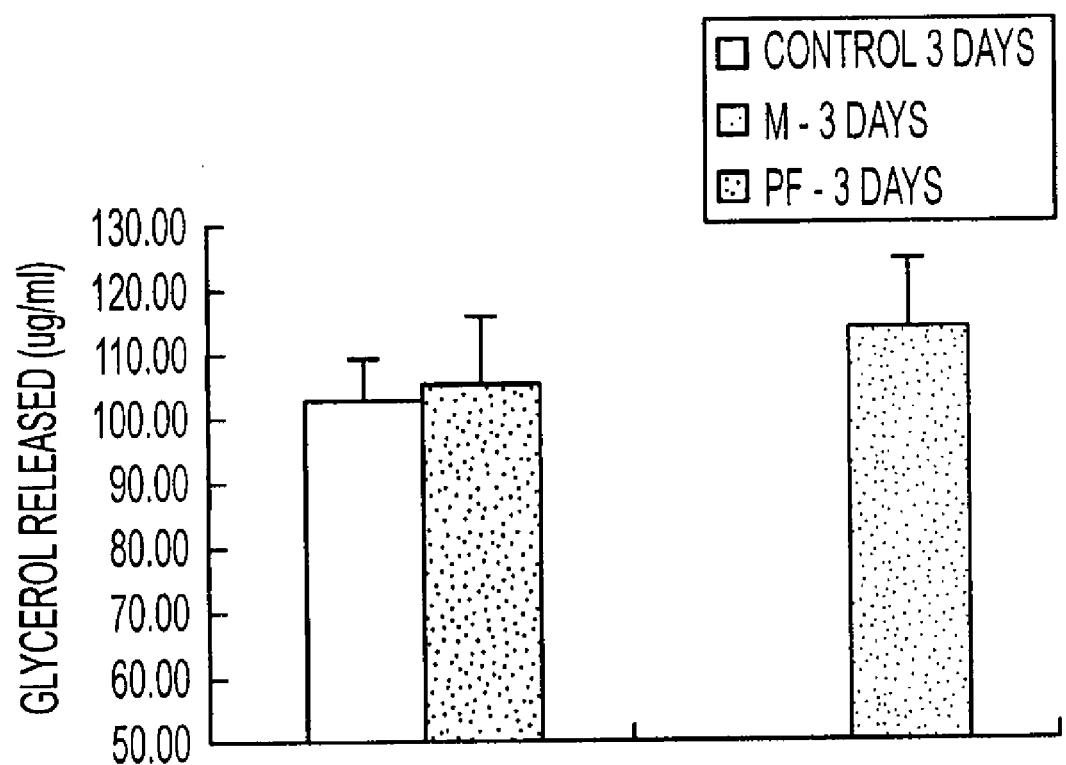
FIG. 12 demonstrates glycerol release after incubation for 3 days with Mesotheraphy (M) and PF.
Figure 13:
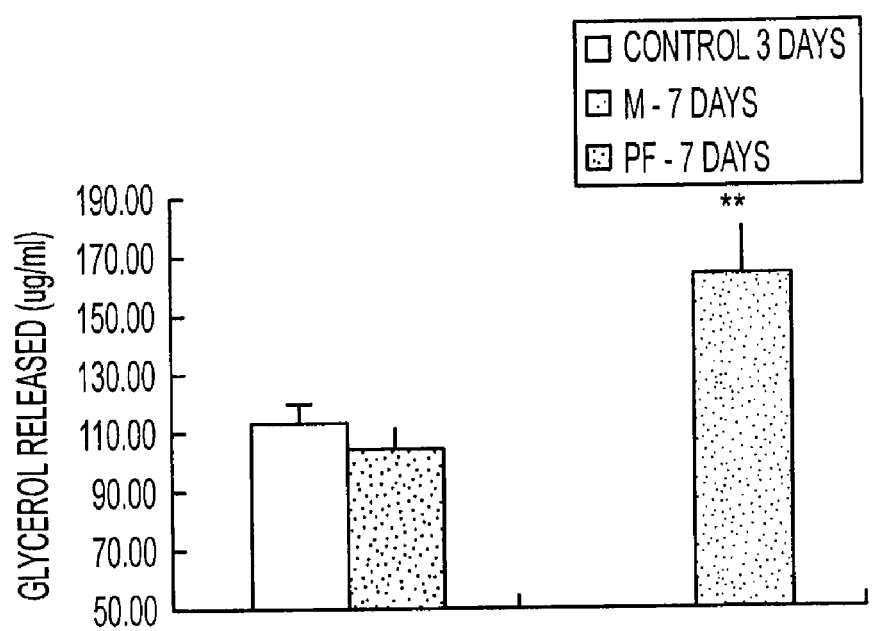
FIG. 13 demonstrates glycerol release after incubation for 7 days with Meso (M) and PF. PF increased the release of glycerol significantly by the $7^{th}$ day after stimulation ($p<0.01$).
Figure 14:
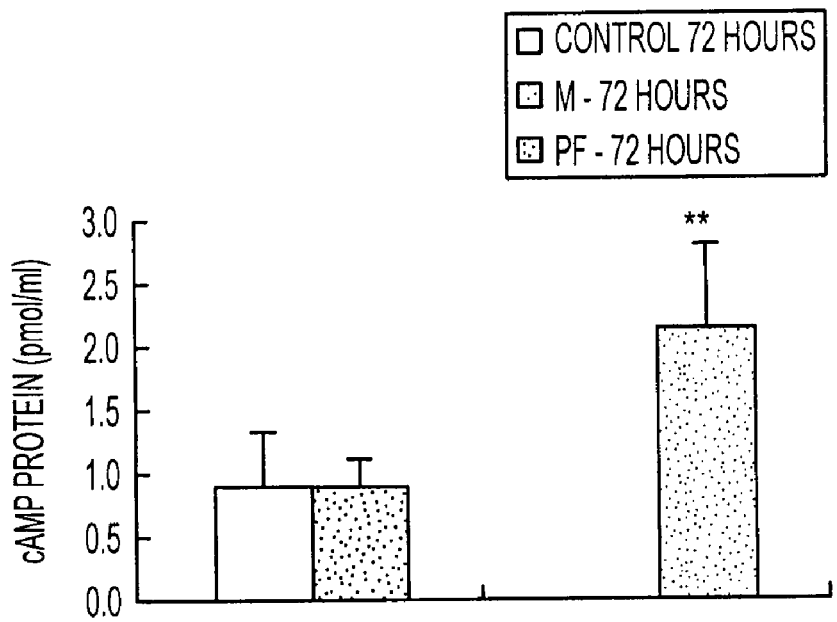
FIG. 14 illustrates intracellular cAMP levels measured by ELISA after incubation with Meso (M) and PF for 72 hours. In the PF group, intracellular cyclic AMP was significantly increased by PF in the first day of stimulation ($p<0.01$). In the M group, the level of cAMP did not show much difference compared to the control group.
Figure 15:
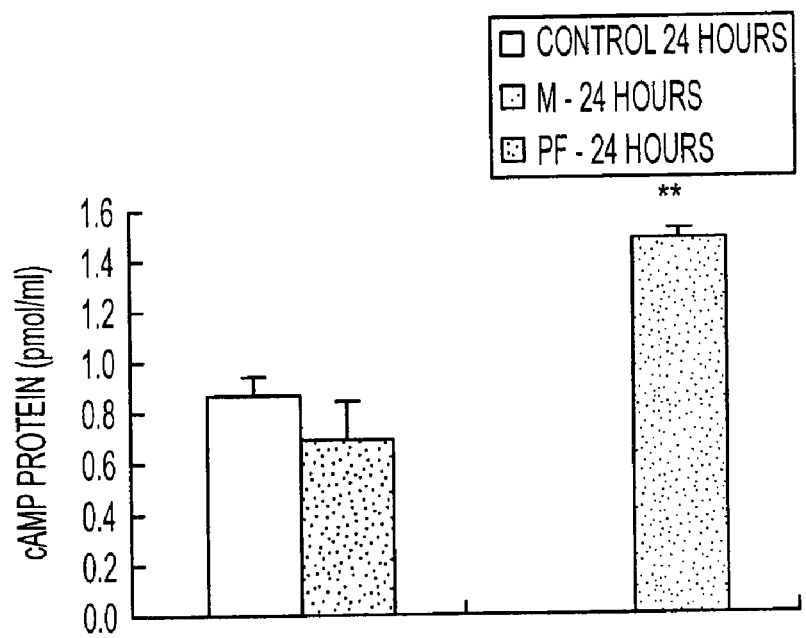
FIG. 15 present results of ELISA demonstrating the intracellular cAMP after incubation of fat cells (adipocytes) with Meso (M) and FF for 24 hours. In the PF group, intracellular cyclic AMP was significantly increased by PF in the first day of stimulation ($p<0.01$). In the Meso group (M), the level of cAMP did not show much difference compared to the control group.
Figure 16:
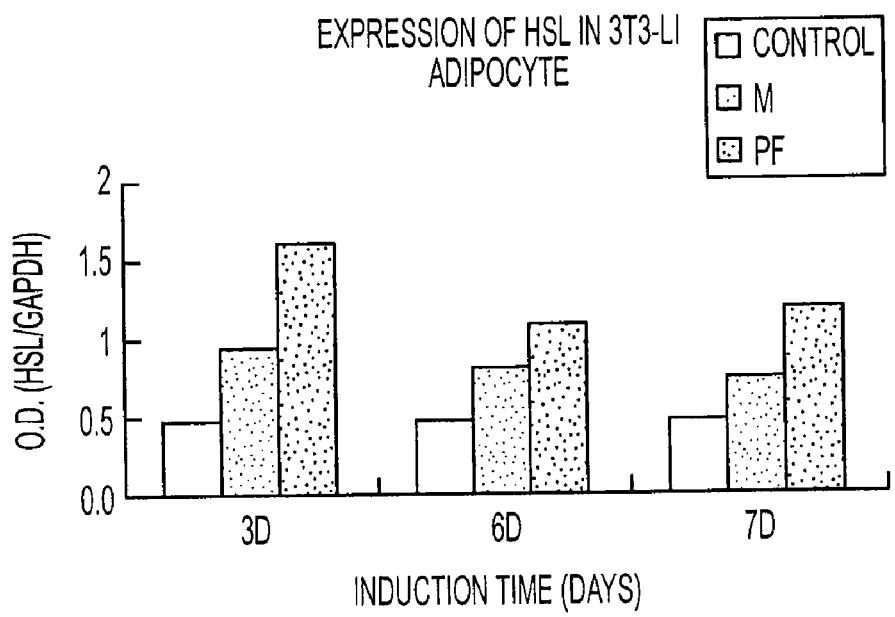
FIG. 16 presents the expression of HSL in 3T3-L1 adipocytes after incubation with Meso (M) and PF. PF increased the expression of HSL in 3T3-L1 adipocytes from the third day after stimulation.

The present example demonstrates that the effect of PF and mesotheraphy (M) on fat cells is distinct from one another. The present example particularly demonstrates that the mode of action of PF on lipolysis is distinct from the action of mesotheraphy. PF breaks down fat by activating fat cells to express more β-adrenergic receptors responsible for fat metabolism. Breaking down fat by PF is accompanied by an increase in cAMP. The increase in cAMP in turn increases the level of expression of HSL, which breaks down fat and causes a significant increase in glycerol released as a result of breaking down triglycerides into glycerol and fatty acids (See FIG. 12—Glycerol release after incubation for 3 days with Meso (M) and PF). Mesotheraphy, on the other hand showed no effect on most of the measured parameters, except on slightly enhancing the HSL as a result of the presence of aminophyline, which is known to act on β-adrenergic receptors.

There is evidenced a significant release of hormone sensitive lipase (HSL) when fat cells are exposed to PF. There is not a significant release of HSL upon Mesotherapy. The present application includes data in the attached figures that establishes that the use of PF results in a release of glycerol from fat cells, that a resulting increase in cAMP occurs and that an increase in hormone sensitive lipase (HSL) occurs. These events did not occur with mesotheraphy, and/or did not occur to the extent evidenced with PF, in comparison to control cultures (no drug added) or with mesotheraphy.

There is evidenced a significant increase in the expression of Adrb1, Adrb2 and Adrb3, and no influence on Adra2b, with exposure to PF. Adrb1 was activated earlier followed by Adbr3, then Adbr2. Adrb2 and Adrb3 were increased by 7.4 fold and 5.65 fold, respectively, at 7 days post exposure to PF. Since the expression of Adra2b almost did not change, while there was significant increase in the βreceptor levels, the ratio of β-adrenergic receptors to a2b-adrenergic receptors is increased by PF. Lipolysis therefore exceeds lipogenesis upon exposure to PF. The data presented herein compares the effects of PF as contrasted to the effects of mesotheraphy and control treatments on cultures of 3T3 cells. This data demonstrates that activation of the intracellular pathway can only be triggered or induced by the activation of the beta adrenergic receptors, and that activation of the beta adrenergic receptors was only achieved with PF exposure, and there was no activation of beta adrenergic receptors with other treatments.

Example 7

In Vivo Clinical Data

The present example demonstrates that the present formulations of PF as part of an injectable preparation effectively provide for targeted fat reduction in a human.

Figure 10:
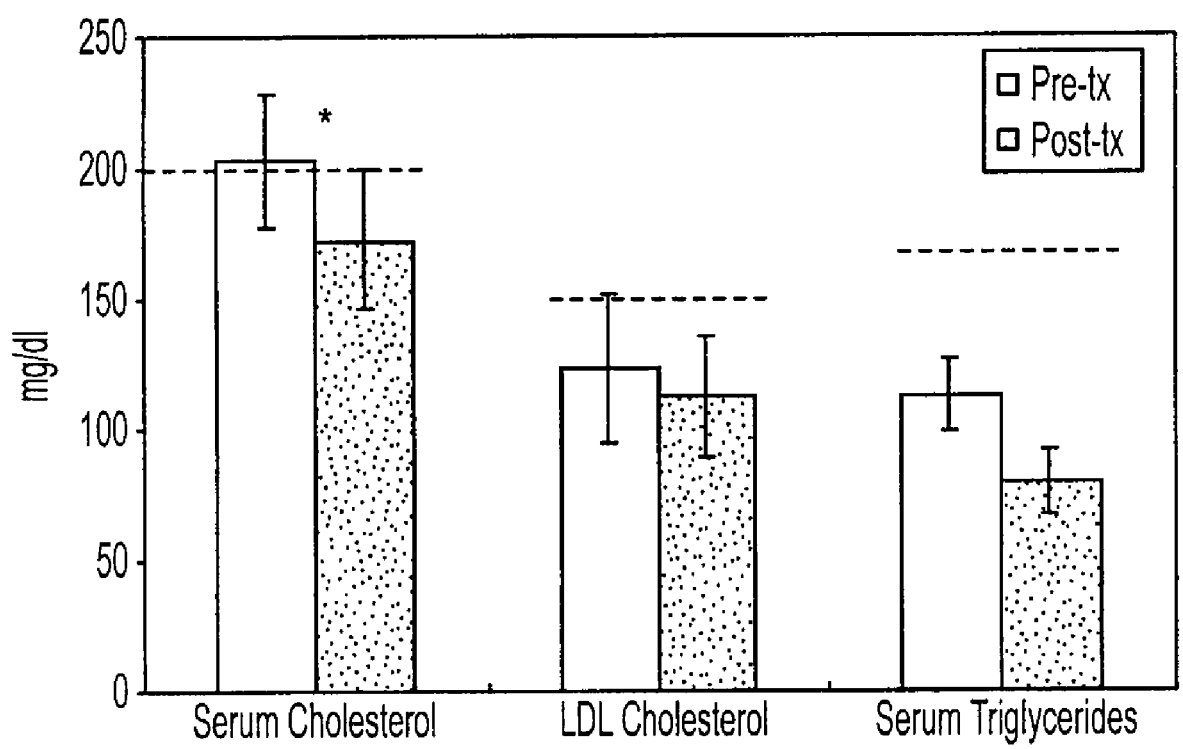
FIG. 10 demonstrates the clinical effect: Comparison of PF. Serum cholesterol, LDL, Cholesterol, serum triglycerides in blood of eight patients was reduced after PF treatment.

Eight patients were treated with PF. The levels of three indices such as serum cholesterol, LDL Cholesterol, serum triglycerides in blood were tested before and after treatment. Serum cholesterol, LDL Cholesterol, serum triglycerides in blood for the eight patients were reduced after PF treatment (Table 6, FIG. 10). For serum cholesterol, the average level for these cases was higher than the high limit of normal range, and the average level fell into normal range after treatment, which showed significant change statistically (P<0.01). For LDL Cholesterol, serum triglycerides, although the change of pre-treatment and post-treatment does not show statistical change, the extent of decrease is meaningful at clinical aspect.

In human, PF has been found to dissolve 1 cm of fat per 1-1.5 sessions in the stomach and thigh areas while about 1 cm per session was observed in the upper arms areas. In almost all the patients, the total cholesterol blood levels were reduced significantly with the PF treatment.

The average level of cholesterol in these cases was higher than the high limit of normal range, and the average level fell into normal range after treatment, which showed statistically significant change (P<0.01).

TABLE 6

Clinical effect comparison of PF

| Case No. | Serum Cholesterol (mg/dl) Pre-tx NR: 50-200 | Serum Cholesterol (mg/dl) Post-tx NR: 50-200 | LDL Cholesterol (mg/dl) Pre-tx NR: 60-150 | LDL Cholesterol (mg/dl) Post-tx NR: 60-150 | Serum Triglycerides (mg/dl) Pre-tx NR: 35-160 | Serum Triglycerides (mg/dl) Post-tx NR: 35-160 |
|---|---|---|---|---|---|---|
| 1 | 216 | 171 | 123 | 113 | 62 | 73 |
| 2 | 173 | 135 | 109 | 75 | 88 | 60 |
| 3 | 207 | 151 | 142 | 92 | 72 | 59 |
| 4 | 233 | 222 | 93 | 146 | 116 | 67 |
| 5 | 169 | 168 | 72 | 108 | 54 | 71 |
| 6 | 269 | 237 | 208.5 | 176.5 | 83 | 110 |
| 7 | 180 | 150 | 117 | 98 | 70 | 55 |
| 8 | 176 | 148 | 118 | 93 | 90 | 85 |
| Ave | 202.88 | 172.75 | 122.81 | 112.69 | 79.38 | 72.50 |
| SD | 35.37 | 37.05 | 40.41 | 33.07 | 19.38 | 17.89 |
| P | 0.002 | | 0.452 | | 0.462 | |

Example 8

In Vivo Fat Reduction

Examples of actual treatment results are presented below and the periods of treatment. These patients were selected because they represented the results of treatment of different areas in the body (stomach, arms, and thighs).

1) Patient 1: Period of Treatment=6 weeks/11 sessions
   Measurements at the stomach area: Size before start: 90 cm
   Size at End of Treatment: 83 cm
2) Patient 2: Period of Treatment=5 weeks/9 sessions
   Measurements (at the stomach
   area) Size before Start: 96 cm
   Size at End of Tx: 90 cm
3) Patient 3: Period of Treatment=1 month/8 sessions In Both Arms: 8 Sessions in total, (i.e. 4 sessions per side)
   Areas treated: both upper arms
   Size Before Start: 40 cm
   Size at End: 36.5 cm Complete Protocol For the Procedure

I. Injectable Preparations

Preparation of Solution: 1 ml of PF (1) at a concentration of 1 mol is mixed with 4 ml injectable water and 5 ml (phosphatidyl choline (PPC)) prepared from soya bean extract and 5 ml 2% lidocain. A total of 15 ml solution. This solution is mixed together in a 20 ml syringe and the needle is changed to a small insulin needle Gauge 30×½ as shown therein before the actual injections are given.

Mode of Action of the mixture: PF is the active ingredient in the mixture. It acts upon contact with the fat cells in the adipose tissues. Phosphatidyl choline is a mild detergent that will bind to fat and thereby bring PF in contact with fat cells for an extended period of time (between 8-12 hours). The lidocain in the mixture increases vascularization into the injected site thus bring in more blood vessels to clear the dissolved fat byproducts.

A topical anesthetic is usually applied to the site prior to injections by 5-10 minutes.

The solution is then given subcutaneously directly into the fat areas at a dose of 0.5 ml per site totaling 20 injections. These injections are spread out to cover a big surface area, e.g. could be spread out through a whole midsection ("love handle") in case of a larger patient, or if the patient were an average size it could be spread out to cover right and left love handles in one session. For reference, please refer to the patients injected in the thigh and buttocks area, for explanation. This patient was injected with 30 smaller injections of 0.2 ml per site, and they were spread through out the whole outer and inner thigh and buttocks areas on the right side.

Each of these 20 smaller injections comprises a session. On average, a noticeable difference was seen within 4-5 sessions. The initial calculations measured 3 cm of fat loss in 5 sessions. The patient lost over 5 pounds of fat with 10 sessions.

D) Number of Sessions Required by the Patients

Each patient is different, depending on their size and the desired amount of fat to be lost. Each 10 sessions resulted in about 7 cm of fat loss. Active patients and those who followed instructions showed above average fat loss. Some patients needed to sculpture small areas and therefore discontinued treatment when the desired result was achieved. The addition of 2 sessions, together with an aerobic instructor, was also observed to result in a weight loss of over 3 pounds in 2 weeks.

Frequency of Injections

One patient evidenced more than 5 inches of fat loss, received 10 sessions over about 6 weeks. After the desired results were achieved, the patient can receive one session every one to two months for maintenance.

Alternative Mode of Application

Figure 11:
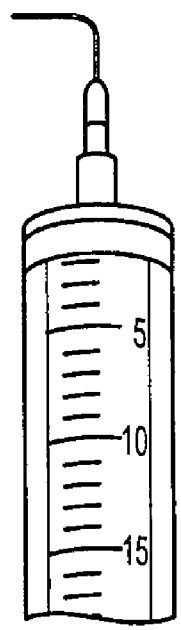
FIG. 11 demonstrates a needle at 90° angle to the long axis of the syringe.

With morbidly obese patients, such as the patient results reported above, the dose of the active ingredient was doubled to 2 ml of 1 mmol in 3 ml of injectable water and mixed with the rest of the solution as mentioned above. A booster injection was used where smaller injections were not appropriate, and the content of one syringe was concentrated into one or two areas of the fat and large needles were used in a retrograde manner of injection. For example, as the needle is pulled out, the injectable solution is released. The needle is rotated in a circular manner to cover a large surface area. It is important to note that the needle is bent to a 90° angle to the long axis of the syringe as shown in FIG. 11.

About 3 ml is injected in this manner, and then the needle is withdrawn, but not totally out of the initial injection site, and re-inserted into another plane at about 30° in a counter clock-wise manner. This process is repeated about 5 times until the content is all injected. For example, employing a circle injection site area to be treated as a targeted fat area, with its center as the initial site of insertion of the needle, then the needle is rotated around this circle in the manner described above.

Concentration ranges of PF included in injectable preparations; doses of PF provided to a patient at each treatment (injection) episode; specific steps that were used in preparing the injectable preparations:

0.5 mg of PF was dissolved in 5 ml of injectable water rendering a concentration of 0.1 mg/ml. This was then mixed with 5 ml of Phosphatidyl Choline in a 20 ml syringe. The large gauge needle was then replaced with a smaller gauge (Guage 27-30, in some embodiments, a 30 guage×½) insulin needle and the 10 ml was injected into 20 different sites of a given area. 0.5 ml of the solution was injected into the stomach, with about 1 cm separating each injection site.

Concentration of PF included into the topical preparation: 0.2 mg to 0.3 mg of PF were dissolved in 1 ml of azone liquid.

This mixture was then massaged into the target area. Azone has been extensively studied using a range of permeates. The composition of the azone is $C_{18}H_{35}NO$. It is colorless, slightly yellowish or transparent in color, and is oil based. Heavy metal content in this compound is less than 0.001%. The azone used in the present studies was purchased from Nan Jing Long Tan chemical company, China. Azone has been shown to enhance permeability through the skin by disrupting the organized lipid structure in the intercellular region of the stratum corneum. This process leads to increased lipid fluidity and enhanced drug diffusion. This is the reason azone was chosen to be mixed with PF.

A low current of 2.5 amp is then passed through pads placed on the skin of the desired treatment area which then drives the PF through the skin into the adipose tissues, thus allowing the PF to come in contact with the fat cells.

Protocol used in creating Albumin Nanospheres.

Many different preparations of nanospheres will be used in the preparations of the present crèmes and topical preparations. Any number of different nanosphere formulations known to those of skill in the art may be used in the practice of the present invention. By way of example, such include any known delivery in the area of nanospheres.

Patient Preparation

For Regular Injections: After sterilization of the surface area with 74% ethanol, topical application of lignocain ointment or lidocain gel was applied for 5 minutes to numb the skin where the injections are to take place.

For Booster Injection

The patient is prepared using 1 ml of 2% lidocain to anaesthetize the site of entry of the large needle. This way, the procedure is almost painless. 3-5 minutes later, the booster injection is given slowly over a 3 minute period.

The patient should ingest a meal before the session, or is provided a chocolate bar or a cookie before a session.

Patients are forewarned that bruising may occur due to the injections. Thus, some bruising in a patient may be expected. For example, bruising was observed in a patient injected in the thighs. The bruising usually disappears within 1 week. In addition, redness and tenderness at the injection site of the booster, is very common. Redness lasts for a couple of hours and the tenderness lasts for a couple of days. Bruising, is encountered more with the booster than the regular injections, but also disappears within a week or so. Another observation is fatigue as a result of treatment in some patients. Two patients suffered from fatigue, with the booster session, but not with the regular session. In addition, a very slight rise in temperature, to about 37.1 or 37.2 for a few hours, was noted. Dizziness for a few minutes was also observed in a few patients, and the adjustable patient chair was reclined and the procedure was continued uneventfully. No diarrhea was observed, but softer stool was reported.

Protocol after the Sessions

A) Patients are asked to drink 2 liters of water per day throughout the day.

B) Patients were asked to walk or exercise for 25 minutes/day for the week after each session. This is intended to flush out dissolved fat byproducts.

C) Avoid fatty diet, wine, alcohol, for the first 48 hrs after the injections, to allow the blood to carry more of the fat byproducts to be excreted.

II. A Second Mode of Application

Crème Preparations

The present preparations may be provided in the form of a crème containing 1 ml of PF at a concentration of 1 mmol mixed with 1 ml of azone which is then massaged into the target area. Azone has been extensively studied using a range of permeants. Azone has been shown to enhance permeability through the skin by disrupting the organized lipid structure in the intercellular region of the stratum corneum. This process leads to increased lipid fluidity and enhanced drug diffusion. This is the reason PF was mixed with azone. Furthermore, a low current is then passed through the tissue area, which then drives the PF through the skin into the adipose tissues. PF may in this way come in contact with fat cells. The clinical results are show below and the details of each patient is documented.

| PATIENT | AGE | SEX | NUMBER OF TIMES | AMOUNT OF REDUCTION IN CM |
|---|---|---|---|---|
| #1 | 37 | M | 6 | 3.5 cm above and below the umbilicus. |
| #2 | 40 | F | 16 | 9 cm above the umbilicus. 9 cm from |

-continued

| PATIENT | AGE | SEX | NUMBER OF TIMES | AMOUNT OF REDUCTION IN CM |
|---|---|---|---|---|
| | | | | midsection. 8 cm from waist |
| #3 | 19 | F | 6 | 2 cm from each side of the upper thigh. |
| #4 | 32 | F | 7 | 8 cm from the right buttock & 9 cm from the left buttock. |
| #5 | 25 | F | 8 | 9 & 10 cm from each leg below the knees. |
| #6 | 44 | F | 12 | 7 cm above umbilicus and 10 cm from midsection |
| #7 | 19 | F | 9 | 6 cm from left thigh and 8 cm from right thigh |
| #8 | 24 | F | 30 | 1.5 size in bra size |
| #9 | 44 | F | 20 | 6 cm above umbilicus and 9 cm below umbilicus. |
| #10 | 44 | F | 20 | 5 cm from the waist and 5 cm from midsection. |
| #11 | 38 | F | 16 | 10 cm above the umbilicus, 9.5 cm below the umbilicus and 5 cm from mid-section (love-handles) |
| #12 | 30 | F | 8 | 10 cm from love handles and 6 cm below the umbilicus. |

III. Alternative Injection Protocol

The present example illustrates an alternative series of treatments that will comprise a treatment session for targeted fat reduction using the injectable preparation and/or composition of PF. In this example, a series of 20 small (0.1 to 0.2 ml) injections comprises a session of treatment. On average, a noticeable difference can be seen in a patient, as evidenced by a reduction in size, within 4 to 5 sessions. The measurable fat loss was 3 cm of fat loss in 5 sessions.

In eight patients treated with PF as described here, the levels of 3 indices such as serum cholesterol, LDL cholesterol, serum triglycerides in the blood were examined before and after treatment. All of these cholesterol parameters were reduced in these eight patient.

In a prior study with Mesotherapy, these cholesterol levels in blood were not reduced (Hexsel, Serra et al 2003).

For serum cholesterol, the average level for these cases was higher than the high limit of a normal range, and the average fell into normal range after treatment, which showed a statistically significant change. ($p<0.01$). For LDL cholesterol, serum triglycerides, although the change of pre-treatment and post-treatment did not show a statistically significant change, the extent of decrease was clinically meaningful in the management of the patient.

Example 9

Delivery Devices

The present example described particular devices and apparatus that may be used in the delivery and application of the various PF topical preparations and injectable preparations of the present invention.

Sauna belt: Uzap tummy, butt, thighs (osim)
Input 100-240 V about 56 Hz
1.5 A 200VA
Output +24V −2.5 A
It has a remote with the following details:
Power consumption 60 W
Operating voltage 24V d.c. 2.5 A
Alpha wave healthtronic muscle stimulator and exercise (the device that transmits electrical current to the pads and is used after/before application of the PF containing crème)
Model BM-303
Power supply DC6V (batteries UM-1×4)
Watts 0.6
Injection Device: Syringe Barrel with 90° angle needle.
Concentration ranges of PF included in injectable preparations. Dose:
Specific steps that were used in preparing the injectable preparations: 0.5 mg of PF was dissolved in 5 ml of injectable water rendering a concentration of 0.1 mg/ml. This was then mixed with 5 ml of Phosphatidyl Choline in a 20 ml syringe. The large needle was then replaced with a smaller gauge insulin needle and the 10 ml was injected into 20 different sites of a given area. 0.5 ml of the solution was injected into the stomach with about 1 cm separating each injection site.
Concentration of PF included into the topical preparation: 0.2 mg to 0.3 mg of PF were dissolved in 1 ml of "Azone liquid". This mixture was then massaged into the target area. Azone has been extensively studied using a range of permeates. The chemical formula for azone is $C_{18}H_{35}NO$. It is colorless, slightly yellowish, or transparent, and is oil based. Heavy metal content in this compound is less than 0.001%. Azone for the present study was purchased from Nan Jing Long Tan chemical company, China. Azone has been shown to enhance permeability through the skin by disrupting the organized lipid structure in the intercellular region of the stratum corneum. This process leads to increased lipid fluidity and enhanced drug diffusivity. This is the reason PF was chosen to be mixed with azone. A low current of 2.5 Amp is then passed through pads placed on the skin of the desired treatment area, which then drives the PF of the crème/lotion through the skin into the adipose tissues. In this manner, PF is allowed to come in contact with the fat cells.

Example 10

Nanosphere Formulations

Many different preparations of nanospheres may be used in the practice of the present preparations and compositions. The most effective formulations will then be identified.

Solid lipid nanoparticles (SLN) and nanostructured lipid carriers (NLC) for the topical application to the skin are made of lipids such as glycerol behenate (Compritol 888 ATO), glycerol palmitostearate (Percirol ATO 5), or the wax, acetyl palmitate. For NLC, at room temperature liquid lipids such as medium chain triglycerides (Miglyol 812) are added. Alternatively, oleic acid belonging to the frequently used penetration enhancers in semisolid vehicles applied to the skin may enhance drug uptake further. Mean particle size ranges from 50 to 1000 nm. Nanodipsersions contain 5 to 40% lipid. The higher concentrated preparations are of semisolid appearance and are cosmetically acceptable as they are. Depending on the mode and concentration of the lipid, 0.5 to 5% surfactant have to be added for physical stabilization of the particles. For dermal use, the preparations may also include, by way of example, the following: Poloxamer 188; Polysorbate 80; Lecithin; Tyloxapol; TegoCare 450 (polyglycerol methylglucose distearate); Miranol Ulta C32 (sodium cocoamphoacetater); or saccharose fatty acid ester.

To facilitate dermal application, fluid dispersions which are obtained when the lipid content is low (<10%) can be incorporated into a crème or gel base which does not include dissolution or aggregation of SLN particles. Photon correlation spectroscopy and differential scanning Calorimetry results have not changed over a storage period of 6 months.

Example 11

Fat Reduction Kits

Component Pieces that would be a part of a kit according to the present example include:
1. 1 ml ampule of PF and Azone at a concentration of 0.2 mg/ml
2. A device like the Alpha Wave healthtronic muscle stimulator & exercise. This a small device used by physiotherapist to stimulate muscles after a sports injury by passing a low density current that causes muscle contraction. Due to the low voltage current of about 2.5 Amp, a current will be transmitted that will drive the PF through the skin and into the adipose tissue after the azone disrupted the organized lipid layer.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

BIBLIOGRAPHY

The following references are specifically incorporated herein by reference.

Asaadi, M., A. P. Salas, et al. (2004). Mesoplasty: a new approach to non-surgical liposculpture. American Society of Plastic Surgery, Philadelphia, Pa., Oct. 9 to 13, 2004.

Ablon G. Preliminary experience with mesotherapy utilizing phosphatidylcholine. American Society for Dermatologic Surgery-American College of Mohsmicrographic surgery and cutaneous oncology combined annual meeting, 2005.

Rittes, P. G. (2001). Dermatologic Surgery 27(4): 391-392

Hexsel, D., M. Serra, et al. (2003). J Drugs Dermatol 2(5): 511-8.

Guedes Rittes, P. (2003). Aesthetic Plastic Surgery 27(4): 315-318.

Rotunda, A. M. (2004). Journal of the American Academy of Dermatology 50(3S): 160-160.

Rotunda, A. M., H. Suzuki, et al. (2004). Dermatologic Surgery 30(7): 1001-1008.

Moy L S. Phosphatidylcholine injections. A study measuring decreased subcutaneous fat thickness. American Society for Dermatologic Surgery and the American Society of Mohsmocrographic surgery and cutaneous oncology combined annual meeting, San Diego, Calif., Sep. 30 to Oct. 3, 2004.

Rullan P, Hexsel D. Phosphatidylcholine injections for lipolysis of neck and jowls: 50 case presentation. American Society for Dermatologic Surgery-American College of Mohs micrographic surgery and cutaneous oncology combined annual meeting, Oct. 27 to 31, 2005.

Duncan, D. I. and F. Hasengschwandtner (2005). Aesthetic Surgery Journal 25(5): 530-543.

EP1748780/WO2005112942

EP1021191/WO9917712

Duncan, et al (2005) *Aesthetic Surgery*, 25(5):530-543.

Hexsel, et al (2005) *Otolaryngologic Clinics of North America*, 38(5):119-29.

Jones, et al (1999) *International Journal of Pharmaceutics* 177(2): 137-159.

Le Maire, et al (2000) *BBA-Biomembrances* 1508 (1-2): 86-111.

Navder (1997) *Life Sciences* 61(19): 1907-1914.

Rittes (2001) *Dermatologic Surgery* 27(4): 391-392.

Rose, et al (2005) *Journal of Cosmetic and Laser Therapy*, 7(1):17-19.

Salti, et al (2007) *Dermatologic Surgery*, 34(1):60-66.

Vedamurthy (2007) *Indian J Dermatol Venereol Leprol* 73(1): 60-2.

Jenning, et al (2000) *International Journal of Pharmaceutics* 199(2): 167-177.

Lombardi, et al (2005) *Journal of Controlled Release* 110(1): 151-163.

Schafer-Korting, et al (2007) *Advanced Drug Delivery Reviews* 59(6): 427-443.

Wissing, et al (2001) *Pharmazie* 56(10): 783-6.

What is claimed is:

1. A method for achieving specific target body area fat loss in a human comprising:
    administering to a targeted area of the body in one or more treatment sessions of an adipolysis enhancing preparation comprising as an active ingredient a purified paeoniflorin in an adipolysis enhancing amount;
    until adipolysis is achieved in the target area.

2. The method of claim 1 wherein the adipolysis enhancing preparation is an injectable preparation.

3. The method of claim 2 wherein the targeted body area receives up to 30 treatment sessions of multiple individual injections, each treatment session comprising an injection of an amount of the adipolysis enhancing preparation of about 0.5 ml to about 1.0 ml.

4. The method of claim 1 wherein the adipolysis enhancing preparation comprises a crème or lotion.

5. The method of claim 1 wherein a low current ultrasound is provided at the skin surface of the targeted body area to be treated before, during, or after, or a combination of before, during or after, administration of the adipolysis enhancing preparation to the skin surface of the targeted body area.

* * * * *